(12) United States Patent
Finke et al.

(10) Patent No.: US 9,327,975 B2
(45) Date of Patent: May 3, 2016

(54) METHOD FOR OBTAINING DINITROGEN OXIDE

(75) Inventors: Thomas Finke, Ettlingen (DE); Ulrich Finke, Schluchsee-Blasiwald (DE)

(73) Assignee: Thomas Finke, Nuertingen (DE)

( * ) Notice: Subject to any disclaimer, the term of this patent is extended or adjusted under 35 U.S.C. 154(b) by 0 days.

(21) Appl. No.: 13/143,712

(22) PCT Filed: Jan. 7, 2010

(86) PCT No.: PCT/EP2010/050102
§ 371 (c)(1),
(2), (4) Date: Oct. 11, 2011

(87) PCT Pub. No.: WO2010/079196
PCT Pub. Date: Jul. 15, 2010

(65) Prior Publication Data
US 2012/0021312 A1    Jan. 26, 2012

(30) Foreign Application Priority Data
Jan. 8, 2009   (DE) .................. 10 2009 000 075

(51) Int. Cl.
| | |
|---|---|
| C01B 21/22 | (2006.01) |
| C02F 1/68 | (2006.01) |
| C02F 1/70 | (2006.01) |
| C02F 3/30 | (2006.01) |
| C12P 3/00 | (2006.01) |

(52) U.S. Cl.
CPC . *C01B 21/22* (2013.01); *C12P 3/00* (2013.01); *B01D 2257/402* (2013.01); *C02F 1/683* (2013.01); *C02F 1/705* (2013.01); *C02F 3/302* (2013.01); *Y02E 50/343* (2013.01)

(58) Field of Classification Search
CPC ........................................ C01B 21/22
USPC ................... 423/400, 402, 405; 435/168
See application file for complete search history.

(56) References Cited

U.S. PATENT DOCUMENTS

| | | | | |
|---|---|---|---|---|
| 3,656,899 | A | * | 4/1972 | Baechle et al. ............... 423/402 |
| 4,173,531 | A | * | 11/1979 | Matsch et al. ............... 210/624 |
| 6,210,649 | B1 | | 4/2001 | Ying et al. |
| 2005/0081827 | A1 | * | 4/2005 | Grant ............................ 123/470 |

FOREIGN PATENT DOCUMENTS

| | | |
|---|---|---|
| CN | 1280519 | 1/2001 |
| CN | 101239753 | 8/2008 |
| DE | 100 50 906 | 4/2002 |
| EP | 1 036 761 | 9/2000 |
| JP | 2001-29989 | 2/2001 |
| JP | 2001-29990 | 2/2001 |
| JP | 2004008923 | 1/2004 |

OTHER PUBLICATIONS

Otte et al, "Nitrous Oxide Production by Alcaligenes faecalis under Transient and Dynamic Aerobic and Anaerobic Conditions," 1996, Appl. Environ. Microbiol. vol. 62, No. 7, pp. 2421-2426.*
Balderston et al, "Blockage by Acetylene of Nitrous Oxide Reduction in Pseudomonas perfectomarinus," (1976), Applied and Environmental Microbiology, vol. 31, No. 4, pp. 504-506.*
Yoshinari, T. et al., Acetylene Inhibition of Nitrous Oxide Reduction and Measurement of Denitrification and Nitrogen Fixation in Soil, Soil Bio. Biochem., vol. 9, 1977, p. 177-183, ISSN:0038-0717.
Park, K.Y. et al., Emission and Control of Nitrous Oxide from a Biological Wastewater Treatment System with Intermittent Aeration, J. of Bioscience and Bioengineering, vol. 90, No. 3, p. 247-252, 2000, ISSN:1389-1723.
Hwang, S. et al., Factors Affecting Nitrous Oxide Production: A Comparison of Biological Nitrogen Removal Processes With Partial and Complete Nitrification, Biodegradation, vol. 17, 2006, p. 19-29, ISSN: 0923-9820.
Hanaki, K. et al., Production of Nitrous Oxide Gas During Denitrification of Wastewater, Water Sci. Tech., vol. 26, No. 5-6, p. 1027-1032, 1992, ISSN: 0273-1223.
Thörn, M. et al., Variation of Nitrous Oxide Formation in the Denitrification Basin in a Wastewater Treatment Plant with Nitrogen Removal, Waster Res., vol. 30, No. 6, p. 1543-1547, ISSN:0043-1354.
Geywitz-Hetz, S. et al., Influence of Some Environmental Conditions on $N_2O$-Release by Activated Sludge under Anoxic Conditions, Hydrobiol., vol. 21, No. 5, 1993, p. 258-266, ISSN:0323-43205.
Knowles, R., Denitrification, Microbiol., vol. 46, No. 1, 1982, p. 43-70, ISSN:0146-0749.
Manconi, I. et al., Effect of Copper Dosing on Sulfide Inhibited Reduction of Nitric and Nitrous Oxide, vol. 15, No. 4, Dec. 2006, p. 400-407, ISSN:1089-8603.
Richardson, D. et al., Mitigating Release of the Potent Greenhouse Gas $N_2O$ from the Nitrogen Cycle—Could Enzymic Regulation Hold the Key?, Trends in Biotechnology, Elsevier Publications, Cambridge, GB LNKD-DOI:10.1016/J.Tibtech., Jul. 1, 2009, p. 388-397, ISSN:0167-7799.
International Search Report for PCT/EP2010/050102, dated Sep. 21, 2010.

* cited by examiner

*Primary Examiner* — Anthony J Zimmer
*Assistant Examiner* — Justin Bova
(74) *Attorney, Agent, or Firm* — Michael J. Striker

(57) ABSTRACT

A method is disclosed for obtaining dinitrogen monoxide by stepwise reduction of nitrates and/or nitrites from substances containing nitrate and/or nitrite, the reduction reaction being interrupted or limited after the step in which the dinitrogen monoxide is formed and the dinitrogen monoxide produced in the reduction reaction being separated, captured and/or collected.

10 Claims, No Drawings

METHOD FOR OBTAINING DINITROGEN OXIDE

FIELD OF THE INVENTION

The present invention relates to a method for obtaining dinitrogen oxide by stepwise reduction of nitrates and/or nitrites from substances containing nitrate and/or nitrite.

BACKGROUND

Substances containing nitrate and/or nitrite are, for example, domestic waste waters such as those purified in sewage treatment plants. To this end, microorganisms are normally used in sewage treatment plants and initially convert nitrates into nitrites in a stepwise reduction. In another reaction, the nitrites are converted into nitrogen monoxide. The nitrogen monoxide reacts further to form dinitrogen monoxide which is reduced further to nitrogen by using suitable reductases. This process is generally referred to as denitrification.

Dinitrogen monoxide, which is also referred to as laughing gas and is used, for example, as an oxidant for combustion processes, for example, in rocket propulsion systems, or as an anesthetic, is generally manufactured presently by catalytic oxidation of ammonia or thermal decomposition of ammonium nitrate. The manufacture is generally complex with respect to energy and technology.

SUMMARY AND DETAILED DESCRIPTION

In a method according to the present invention for obtaining dinitrogen monoxide by stepwise reduction of nitrates and/or nitrites from substances containing nitrate and/or nitrite, the reduction reaction is interrupted or limited after the step in which the dinitrogen monoxide is formed. Dinitrogen monoxide produced in the reduction reaction is separated, captured and/or collected.

Within the meaning of the present invention, substances containing nitrate and/or nitrite are all substances in which nitrates and/or nitrites are broken down during processing. These are, for example, waste waters or also liquids or slurries occurring in agriculture, for example, liquid manure, or also wastes, in particular wastes or substances occurring, for example, in the production of biogas.

An advantage of the method according to the present invention is that the manufacture of dinitrogen monoxide is coupled with the processing of substances containing nitrate and/or nitrite. Since dinitrogen monoxide occurs as an intermediate product during the processing of substances containing nitrate and/or nitrite, a favorable method for favorably producing dinitrogen monoxide may be implemented in this way by completely or partially suppressing the reduction step in which dinitrogen monoxide is reduced to nitrogen.

According to the present invention, the stepwise reduction of nitrates and/or nitrites is a biological decomposition of nitrates and/or nitrites from substances containing nitrate and/or nitrite, nitrate initially being reduced to nitrite which is further reduced to nitrogen monoxide and the nitrogen monoxide is then reduced to dinitrogen monoxide. In the methods currently used, the dinitrogen monoxide is reduced further to nitrogen. This reduction of nitrates to nitrogen is also referred to as denitrification.

For the biological decomposition of nitrates and/or nitrites from substances containing nitrate and/or nitrite, suitable microorganisms are used. These microorganisms are also generally referred to as denitrifiers. Heterotrophic and autotrophic bacteria, fungi, parasites and phages are suitable as denitrifiers. Generally, the denitrification capability is widespread within the prokaryotes. Suitable autotrophic bacteria are, for example, *Paracoccus denitrificans* and *Thiobacillus denitrificans*. *Pseudomonas stutzeri* are used, for example as heterotrophic bacteria.

The individual steps of the reduction of the nitrate and/or nitrite to dinitrogen monoxide are catalyzed by suitable metalloenzymes. The metalloenzymes used are nitrate reductase for converting nitrate to nitrate, nitrite reductase for converting the nitrite into nitrogen monoxide and nitrogen monoxide reductase for converting the nitrogen monoxide into dinitrogen monoxide. In conventional methods for purifying waste waters, dinitrogen monoxide reductase participates in the reaction of dinitrogen monoxide to form nitrogen.

For the method according to the present invention, the reduction of the dinitrogen monoxide to nitrogen is completely or partially suppressed. This makes it possible to obtain large quantities of dinitrogen monoxide.

The production of dinitrogen monoxide makes it possible to utilize the chemical energy of nitrogen-containing waste waters in a practical manner. Heretofore, the energy-related utilization of waste water has been limited to the production of biogas or hydrogen based on the organic hydrocarbon compounds contained in the waste water. The method according to the present invention for obtaining dinitrogen monoxide opens up a new method for the energy-related utilization of waste water based on the nitrogen-containing components contained in waste water.

For the production of dinitrogen monoxide, it is preferred to separate it from the liquid and/or gaseous phase. The separation primarily makes it possible to obtain pure dinitrogen monoxide. The purity of the dinitrogen monoxide is a function of the type of processing and separation. In this connection, all gaseous products which occur when the dinitrogen monoxide is obtained by stepwise reduction are referred to as a gaseous phase or as a waste gas. If the dinitrogen monoxide is formed during waste water purification in sewage treatment plants, gaseous hydrocarbons, carbon monoxide, carbon dioxide and components of the ambient air may be contained in addition to the dinitrogen monoxide. Additional gaseous decomposition products from the waste water purification may also be contained in the waste gas. Furthermore, the waste gas from other steps of the waste water purification, for example, the waste gas of the nitrification, may be supplied to the gaseous phase.

In one specific embodiment, the dinitrogen monoxide is, for example, separated from the waste gas by a gas membrane which is selective for dinitrogen monoxide. Such gas membranes which are selective for dinitrogen monoxide are known to those skilled in the art. Alternatively, it also possible to use a gas membrane which is impermeable to dinitrogen monoxide and allows the other components of the gas containing the dinitrogen monoxide to pass through, so that the dinitrogen monoxide is concentrated in the retentate stream.

However, it is also possible, for example, to liquefy the dinitrogen monoxide of the waste gas by, for example, increasing the pressure or reducing the temperature. The liquefied dinitrogen monoxide is separated by condensation, making it possible to collect it.

Other gas purification methods known to those skilled in the art may also be used for separating the dinitrogen monoxide from the waste gas. Such methods are, for example, stripping, membrane, condensation, adsorption, distillation or rectification processes and/or additional known methods for separating and purifying gases. For example, the separation of the dinitrogen monoxide by suitable molecular sieves, by introducing and dissolving the gas containing the dinitrogen monoxide in liquid or solid media are suitable for concentration or selective adsorption processes. Ferrous sulfate solution and ferrous sulfate emulsified in sulfuric acid as well as $P_2O_5$ are, for example, suitable as liquid or solid media through which the gas containing the dinitrogen monoxide is conducted.

This may be followed by rectification, distillation or extraction for additional purification.

Depending on the later use, however, it is also possible to use the dinitrogen monoxide in an unpurified form.

To separate the dinitrogen monoxide from the liquid phase in order, for example, to withdraw the dinitrogen monoxide as a waste gas, gas suction may be used, for example. To this end, it is, for example, possible to apply a covering and perform removal by suction using a vacuum. This makes it possible, for example, to convert the dinitrogen monoxide dissolved in the liquid phase into the gas phase.

In addition to applying a vacuum, the dinitrogen monoxide dissolved in the liquid phase may also be separated, for example, by pressure variation.

It is also possible to remove dinitrogen monoxide dissolved in the liquid phase by, for example, salting out, stripping or driving out using a gas, for example, using air or steam or also using different media known to those skilled in the art.

Alternatively, it is also possible, for example, to convert the dinitrogen monoxide into the gas phase by introducing thermal energy. The introduction of thermal energy reduces the solubility of the dinitrogen monoxide in the liquid. Moreover, a portion of the liquid evaporates. The introduction of the thermal energy may be accomplished by any method known to those skilled in the art. Normally, the thermal energy is applied by heating using a suitable heat exchanger or electric heating. If a heat exchanger is used, it is possible to use, for example, a container having a double jacket, the double jacket being heated. Alternatively, however, any desired heat exchanger element may also be provided in a container in which the liquid containing the dinitrogen monoxide is contained. Such heat exchanger elements are, for example, heat exchanger plates or pipes through which a heat carrier flows. Heat carriers in customary use are, for example, heat transfer oils, water and steam.

After the dinitrogen monoxide is separated out from the liquid phase, another purification may be performed, for example, by using a gas membrane which is selective for dinitrogen monoxide or by liquefying the dinitrogen monoxide, as described above.

The aqueous phase remaining after the dinitrogen monoxide is removed, in which components of dinitrogen monoxide may still remain, may subsequently be supplied to a downstream unmodified complete denitrification process.

To achieve an improved yield of dinitrogen monoxide, it is furthermore possible, for example, to perform a concentration by extraction before the dinitrogen monoxide is separated from the liquid phase.

To prevent or limit the reduction reaction of the dinitrogen monoxide to nitrogen, copper ions of the metalloenzyme used for reducing the dinitrogen monoxide are reduced, removed or complexed before and/or during denitrification. Alternatively, a copper separation may also be performed within the meaning of the present invention using selective ion exchangers before or during denitrification. Furthermore, the dinitrogen monoxide reductase may be completely or partially inhibited before and/or during the denitrification by suitable irreversible and/or reversible or non-competitive and/or competitive inhibitors and/or by substrate inhibition or product inhibition. The method according to the present invention for obtaining dinitrogen monoxide may also be used in this way even with methods currently used for purifying waste waters in a simple way before and/or during denitrification.

The copper ions may be removed and/or complexed before and/or during denitrification, for example, by using complexing agents, by reduction using suitable metals or metal ions and using all redox systems which are capable of completely or partially reducing the copper ions of the present concentration, by selective ion exchangers or by electrochemical reduction, for example, by electrolysis.

Chelating substances, for example, tetra acetyl ethylene diamine (TAED) may be used, for example, as complexing agents of the copper ions. However, sulfonamide-substituted thionoligands, 1-(-chloro-3-indazolyl-azo)-2-hydroxynaphthalene-3,6-disulfonic acid-analog ligands or chlorophyll-based ligands are suitable as complexing agents for removing the copper ions.

Suitable metals that may be used for reducing the copper ions, for example, by sedimentation, are, for example, iron, tin and zinc. Suitable metal ions are, for example, $Sn^{2+}$ ions. Suitable additional redox systems for reducing copper ions are, for example, nitrate and/or nitrite ions in suitable concentration ratios. Iron is preferred in particular.

To remove the copper ions by using selective ion exchangers, it is known to those skilled in the art to use ion exchangers which are selective for copper ions. Suitable ion exchangers are, for example, ones that contain metal ions, for example, calcium, magnesium or sodium ions as the exchange ions, and furthermore chelating and adsorptive ion exchangers. Suitable ion exchangers are, for example, modified sulfonated polystyrene ion exchangers, variously substituted iminodiacetic acid ion exchangers and additional polymer and/or silicate-based ion exchangers.

Within the meaning of the present invention, ion exchangers may also be used as immobilizers of the microorganisms. In this connection, the microorganisms are immobilized by the complexing of the copper ions. The copper complexing produces an inhibiting effect on the dinitrogen monoxide reductase.

Suitable irreversible and/or reversible or non-competitive and/or competitive inhibitors for the method for obtaining dinitrogen monoxide are, for example, substances that deactivate the active center of the dinitrogen monoxide reductase or bind to this center instead of dinitrogen monoxide. Suitable substances in this connection are substances that, for example, have a structural similarity with dinitrogen monoxide, for example, $N_2O$-containing metal complexes.

The complexing agents or the metals, metal ions, additional redox systems and ions or ion exchangers as well as suitable irreversible and/or reversible or non-competitive and/or competitive inhibitors used for sedimentation may, for example, be added to the liquid phase before and/or during denitrification in liquid, solid or gaseous form, granulate and/or plate form.

Alternatively, however, it is also possible, in particular when using an ion exchanger for removing the copper ions, to guide the waste water through a suitable column containing the ion exchanger. In this case, the ion exchanger may be present as a structured or random packing. It is thus possible, for example, for the ion exchanger to be contained in the column in the form of a woven or knitted fabric or also as support medium. It is also possible to fill the column with an ion exchanger granulate. An advantage of using a column is that it is possible to regenerate the ion exchanger in a simple way, for example, by exchange or by switching to a second column which also contains an ion exchanger. It is then possible to regenerate the ion exchanger in the column which is not being used.

In addition to obtaining the dinitrogen monoxide from the purification of waste waters, it is alternatively possible to obtain the dinitrogen monoxide through biological degradation of nitrate and/or nitrite from any other processes. It is thus, for example, also possible to obtain the dinitrogen monoxide from liquids containing nitrate and/or nitrites which occur, for example, in biogas production. Furthermore, in addition to domestic waste waters, it is also possible to use domestic wastes, waste waters, wastes and waste products occurring in industry and agriculture, in particular grain and/or grass waste cuttings, for obtaining dinitrogen monoxide. The dinitrogen monoxide may thus also be obtained, for example, from liquid manure or compost.

The dinitrogen monoxide may also be separated from the biogas according to the method described above.

The dinitrogen monoxide obtained using the method according to the present invention may, for example, be supplied to an oxidation reaction as an oxygen carrier. The use of dinitrogen monoxide as an oxygen carrier makes it possible to improve the energy efficiency of combustion processes significantly compared to oxygen used as an oxygen carrier.

The dinitrogen monoxide may be used, for example, for the combustion of coal, natural gas and fuels in internal combustion engines or in fuel cells. As described above, the use of the dinitrogen monoxide makes it possible to significantly improve the energy efficiency of internal combustion engines and fuel cells. As a result, the energy-specific carbon dioxide emissions are also reduced significantly.

Additional suitable applications of dinitrogen monoxide include application as a fuel and/or oxidant in a combustion system or also use as a reagent in a conversion reaction or continuing synthesis.

What is claimed is:

1. A method for obtaining dinitrogen monoxide, the method comprising:
    stepwise reducing at least one of (a) nitrates and (b) nitrites from substances containing at least one of (a) nitrate and (b) nitrite;
    at least one of (a) interrupting the stepwise reduction after a stage in which a reduction reaction produces dinitrogen monoxide and (b) limiting the stepwise reduction after the stage in which the reduction reaction produces dinitrogen monoxide; and
    at least one of (a) separating the dinitrogen monoxide produced in the reduction reaction, (b) capturing the dinitrogen monoxide produced in the reduction reaction, and (c) collecting the dinitrogen monoxide produced in the reduction reaction;
    wherein the stepwise reducing of the nitrate and/or nitrite to dinitrogen monoxide are catalyzed by metalloenzymes, the metalloenzymes used being nitrate reductase for converting nitrate to nitrite, nitrite reductase for converting the nitrite into nitrogen monoxide and nitrogen monoxide reductase for converting the nitrogen monoxide into dinitrogen monoxide, and
    wherein to interrupt or limit the reduction reaction of the dinitrogen monoxide to nitrogen, copper ions of the metalloenzyme used for reducing the dinitrogen monoxide are reduced, removed or complexed before and/or during denitrification,
    wherein to interrupt or limit the reduction reaction of the dinitrogen monoxide to nitrogen, copper ions of the metalloenzyme used for reducing the dinitrogen monoxide are removed from the metalloenzyme by complexing with a complexing agent and/or complexed within the metalloenzyme by complexing with said complexing agent before and/or during denitrification,
    wherein the complexing agent for removing the copper ions is selected from the group consisting of, sulfonamide-substituted thionoligands, 1-(chloro-3-indazolyl-azo)-2-hydroxy-naphthalene-3,6-disulfonic acid-analog ligands and chlorophyll-based ligands.

2. The method as recited in claim 1, wherein the stepwise reduction is a biological decomposition of at least one of (a) nitrates and (b) nitrites from the substances containing at least one of (a) nitrate and (b) nitrite, nitrate initially being reduced to nitrite which is further reduced to nitrogen monoxide and the nitrogen monoxide then being reduced to dinitrogen monoxide.

3. The method as recited in claim 1, wherein the dinitrogen monoxide is separated from at least one of (a) a liquid phase and/or (b) a waste gas.

4. The method as recited in claim 3, wherein the dinitrogen monoxide is purified by selective membrane processes.

5. The method as recited in claim 2, wherein activity of a dinitrogen monoxide reductase is limited or suspended by at least one of (a) irreversible inhibitors, (b) reversible inhibitors, (c) non-competitive inhibitors, (c) competitive inhibitors, (d) substrate inhibition, and (d) product inhibition.

6. The method as recited in claim 1, wherein the substances containing the at least one of (a) nitrate and (b) nitrite comprise: (a) domestic waste water, (b) domestic wastes, (c) wastes occurring in industry, (d) waste products occurring in industry, (e) wastes occurring in agriculture, or (f) waste products occurring in agriculture.

7. The method as recited in claim 1, wherein the substances containing the at least one of (a) nitrate and (b) nitrite occur in the manufacture of biogas.

8. The method as recited in claim 1, further comprising: supplying the dinitrogen monoxide to an oxidation reaction as an oxygen carrier.

9. The method as recited in claim 8, wherein the oxidation reaction is (a) a combustion of coal, natural gas or fuel in an internal combustion engine or (b) an oxidation reaction in a fuel cell.

10. The method as recited in claim 1, further comprising: supplying the dinitrogen monoxide to a combustion system as at least one of (a) a fuel and (b) an oxidant.

* * * * *